United States Patent

Tantram et al.

[11] Patent Number: 4,474,648
[45] Date of Patent: Oct. 2, 1984

[54] GAS SENSOR

[75] Inventors: Anthony D. S. Tantram, Great Bookham; Bryan S. Hobbs, Chertsey; John R. Finbow, Kempston; Yat S. Chan, London, all of England

[73] Assignee: City Technology Limited, London, England

[21] Appl. No.: 256,283

[22] Filed: Apr. 23, 1981

[30] Foreign Application Priority Data

Apr. 30, 1980 [GB] United Kingdom ............... 8014272

[51] Int. Cl.³ ........................................... G01N 27/46
[52] U.S. Cl. ................................... 204/1 T; 204/415; 204/431
[58] Field of Search ............... 204/1 T, 1 K, 195 R, 204/195 P, 400, 415, 431-433

[56] References Cited

U.S. PATENT DOCUMENTS

| 3,691,023 | 9/1972 | Ruka et al. | 204/1 S |
| 3,719,576 | 3/1973 | Macur | 204/1 K |
| 3,776,832 | 12/1973 | Oswin et al. | 204/1 K |
| 4,132,616 | 1/1979 | Tantram et al. | 204/195 P |
| 4,202,748 | 5/1980 | Kroneisen | 204/1 K |

OTHER PUBLICATIONS

Ives et al., "Reference Electrodes", 1961, pp. 333-336.

Primary Examiner—T. Tung
Attorney, Agent, or Firm—Sughrue, Mion, Zinn, Macpeak & Seas

[57] ABSTRACT

An electro-chemical cell for quantitatively detecting an acidic or an alkaline gas, e.g. carbon dioxide, includes a sensing electrode 9 which is connected to a top cap 12 by a contact strip 8 and is accessible to the gas to be tested through a hole 13. The electrode 9 comprises an electro-chemical couple whose potential is pH-dependent (e.g. silver/silver oxide for carbon dioxide) the active material being supported by a nickel gauze to give good current collection. A counter electrode 2 without significant gas access is immersed in an electrolyte 3 whose pH is such that it will change following adsorption of the gas being tested for. A wicking separator 7 ensures an electrolytic path between the two electrodes. The components are contained within a metal can 1, the top cap 12 being held by folding over the rim 5. An insulating grommet 6 is fitted between the two electrodes. When using silver/silver oxide for the sensing electrode 9, the counter electrode may be of the same material and the electrolyte may be potassium carbonate. The current flowing between the electrodes is a measure of the concentration of gas being detected. A reference electrode 14 may also be included.

12 Claims, 3 Drawing Figures

GAS SENSOR

This invention relates to gas sensors and is particularly concerned with the sensing of acid or alkaline constituents of a gaseous mixture with special reference to the detection and analysis of carbon dioxide. The invention will therefore be described specifically in terms of its applicability to the sensing of carbon dioxide even though the broader, more general application may be equally relevant.

Carbon dioxide sensing devices are required for safety monitors for use where personnel have to work in confined spaces especially where carbon dioxide, additional to that generated by the personnel themselves, may escape, for example in breweries or in atomic power stations, where carbon dioxide is used as a coolant. For personnel safety monitoring small, portable, robust, reliable and easy to use sensors are demanded.

The estimation of carbon dioxide in flue gas is useful for ensuring efficient combustion and its estimation is also important in a number of industrial processes.

Existing methods for monitoring carbon dioxide, e.g. infra-red, thermal conductivity, gas chromatography, mass spectrometry, volume, pressure- or conductivity-change following absorption, all suffer from one or more disadvantages, particularly for safety monitoring applications, e.g. they are either too bulky, too costly, insufficiently sensitive, too slow, inconvenient or difficult to use, needing skilled operators.

According to the present invention a gas sensor for carbon dioxide or other acid and alkaline gases takes the form of an electro-chemical cell including a sensing electrode which is accessible to the gas to be tested and which comprises or is in electrical contact with an electro-chemical couple whose potential is pH dependent, a counter electrode without significant gas access and an electrolyte in contact with both electrodes whose pH is such that it will change following absorption of the gas being tested for. The cell may also include a third reference electrode without significant gas access.

The effect of access of the gas to be tested to the sensing electrode, results in a method of testing in accordance with the invention in which a quantity of the gas is absorbed by the electrolyte in the vicinity of the sensing electrode, thus changing the pH of the electrolyte in this region; this in its turn changes the potential of the sensing electrode and hence the potential difference between the two electrodes which, with a suitable loading circuit connected across the two electrodes, causes a current to flow to redress the imbalance, thus providing a current signal which is dependent on the concentration of the gas under test, e.g. carbon dioxide. When testing for carbon dioxide and operating in the galvanic mode as just described the potential of the sensing electrode tends to rise with decreasing local pH following carbon dioxide absorption and the electrode undergoes a cathodic (reducing) discharge, which generates hydroxyl ions to neutralise the absorbing carbon dioxide. An anodic (oxidising) reaction will occur at the counter electrode.

A particular example is illustrated by the following reactions:

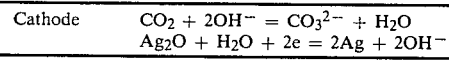

| Cathode | $CO_2 + 2OH^- = CO_3^{2-} + H_2O$ |
| | $Ag_2O + H_2O + 2e = 2Ag + 2OH^-$ | net cathode reaction

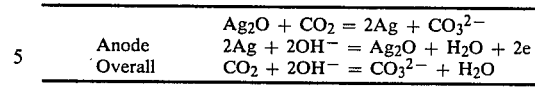

| Anode | $Ag_2O + CO_2 = 2Ag + CO_3^{2-}$ |
| | $2Ag + 2OH^- = Ag_2O + H_2O + 2e$ |
| Overall | $CO_2 + 2OH^- = CO_3^{2-} + H_2O$ |

Expressed more generally, the nature of the discharge at the respective electrodes will depend on whether the gas being tested for is acid or alkaline. When operating in the galvanic mode in this way, the current signal can be readily converted to a voltage signal for instrumental purposes by means of a series resistor.

The requirement that the sensing electrode should comprise or be in electrical contact with an electro-chemical couple whose potential is pH dependent implies the use of a couple where the formation or consumption of either hydroxyl or hydrogen ions is concerned in the electrode reaction. Examples of such couples are $Ag/Ag_2O$; $Hg/HgO$; the nickel hydroxide couple as used in nickel cadmium batteries; in general any metal/metal oxide or metal/hydroxide couple; and certain redox couples which may, for example, be soluble redox couples, such as $I^-/IO_3^-$ and $NO_2^-/NO_3^-$. Since it may be necessary to carry out the monitoring in the presence of air or oxygen, the selected couple should be such as not to produce any interfering signal as a result of oxygen reduction. In other words the nature of the couple or its operating potential should be such as to avoid any significant electro-chemical oxygen reduction at the sensing electrode.

To consider the first of the above examples, the electrode reaction follows the equation

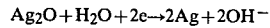

$$Ag_2O + H_2O + 2e \rightarrow 2Ag + 2OH^-$$

The counter electrode may comprise or be in contact with any couple at which an appropriate reaction can occur, i.e. an oxidising reaction in the case of a carbon dioxide or other acidic gas sensor or a reducing reaction in the case of an alkaline gas sensor. The counter electrode couple may be the same as or different from the sensing electrode and may be a soluble redox couple. The couple used may be either pH sensitive or pH insensitive, there being minor advantages and disadvantages of each. Examples of suitable couples are silver/silver oxide; mercury/mercury oxide; lead/lead carbonate; iodide/iodate.

The fundamental requirement in the choice of electrolyte is that the absorption of the gas being tested for should produce a significant local change in a pH at the sensing electrode. Thus in the case of carbon dioxide, the pH of the electrolyte should be greater than 3.6 and preferably within the range 8 to 14. The electrolyte must, of course, be compatible with the materials of the sensing and counter electrodes and, in particular, no chemical reaction should occur. Similar considerations apply to the material to be used for the cell casing.

Useful electrolytes include those, e.g., which contain a solid hydroxide of barium, calcium or magnesium.

Access of gas to the sensing electrode may be provided in any of the well known ways for satisfying a similar requirement in fuel cells. For example, the electrode material may be mixed with particles of PTFE so as to provide hydrophobic gas channels in the body of the electrode. For this purpose, a PTFE dispersion may conveniently be used, this being dried and the wetting agent originally present in the dispersion then being removed either by heat treatment or by solvent extraction. The resulting mixture of electrode particles and PTFE particles may, if required, be applied to a current collector such as nickel gauze and in order to ensure that there is no seepage of electrolyte out of the cell, it is desirable to attach a further layer of porous hydrophobic material, such as PTFE, to the gas side of the electrode.

Suitable sensor designs and construction methods can be adapted from those used in the design and construction of batteries.

An example of a design of cell in accordance with the invention will now be described with reference to the accompanying drawings, in which.

Figure 1:
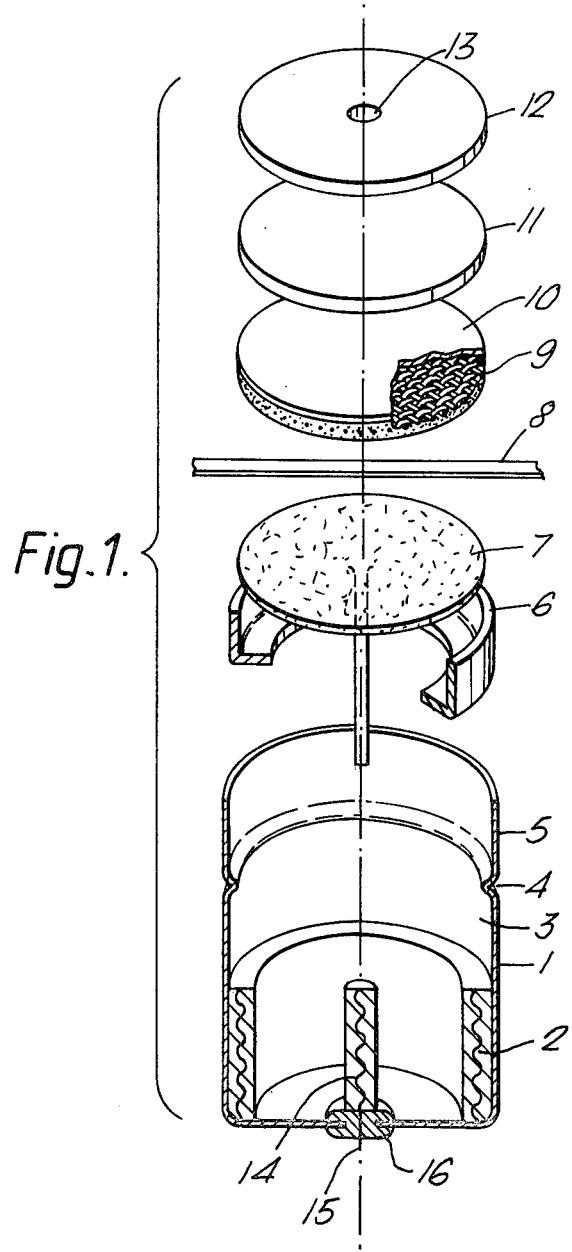
FIG. 1 is an exploded perspective view of the cell.

A metal can 1, for example of nickel plated steel, contains and electrically contacts a counter electrode 2, and is filled approximately to the level of a rill 4 with electrolyte 3. After fitting the top assembly components which are described below, the can may be closed and sealed by folding over the rim 5. The components of the top assembly comprise an insulating grommet seal 6, a wicking separator 7 to ensure an electrolytic path between the two electrodes and a narrow strip 8 of thin metal foil to connect a sensing electrode 9 with a metal top cap 12 on closure. The sensing electrode 9 is waterproofed by a layer 10 of unsintered porous PTFE tape pressed on to the electrode to form a unitary assembly. A porous disc 11, for example of porous plastic, serves to ensure a good spread of gas diffusion over the sensing electrode. The metal top cap 12 contains a gas access hole 13. Restriction to the rate of gas access may be accomplished by restricting the size of the hole 13 or by inter-posing an additional diffusion barrier between 11 and 12. The final electrical connections to the counter and sensing electrodes respectively are made to 1 and 12. The sensing electrode 9 may conveniently be based on a nickel gauze to ensure good current collection, into which the active material is pressed, mixed with PTFE powder to give good gas distribution throughout the electrode. The counter electrode 2 may be made similarly, but in this case it is not necessary to use a hydrophobic binder such as PTFE as with the sensing electrode. The active material referred to above comprises the chosen solid couple, for example $Ag/Ag_2O$, or in other cases, for example when soluble redox couples are used, a catalytic material such as platinum powder.

A reference electrode 14 may be included if required and may have a construction similar to that of the counter electrode 2. An electrical connection 15 to this electrode passes through an insulating seal 16. The purpose of the reference electrode 14 when used with a conventional three electrode potentiostatic circuit, is to maintain the sensing electrode 9 substantially at a constant potential independent of the counter electrode 2.

Good results with relatively high signals (of the order of 10 to 100 micro-amps per $cm^2$ of sensing electrode with 0.5% carbon dioxide) have been obtained, for example by using silver/silver oxide as the active sensing electrode material in conjunction with potassium carbonate electrolyte and silver/silver oxide or lead in the counter electrode. In the latter case, where the counter electrode has a low potential, it has been found advantageous to include a "Cellophane" (registered trade mark) separator, as used in silver/zinc batteries, to cut down self discharge of the silver oxide. Similar results have also been obtained using an electrolyte of potassium acetate mixed with barium hydroxide instead of potassium carbonate.

Good results with relatively lower signals (of the order of 0.1 to 5 micro-amps per $cm^2$ of sensing electrode with 0.5% carbon dioxide), but with indications of a longer useful sensor life have been obtained using electrolytes containing potassium iodide and potassium iodate; potassium nitrite and potassium nitrate; and mixtures of these two soluble redox couples, the pH having in each case been brought up to around 12 to 14 with potassium hydroxide, in conjunction with silver, carbon, platinum, gold as the catalytically active electrode materials.

Figure 2:
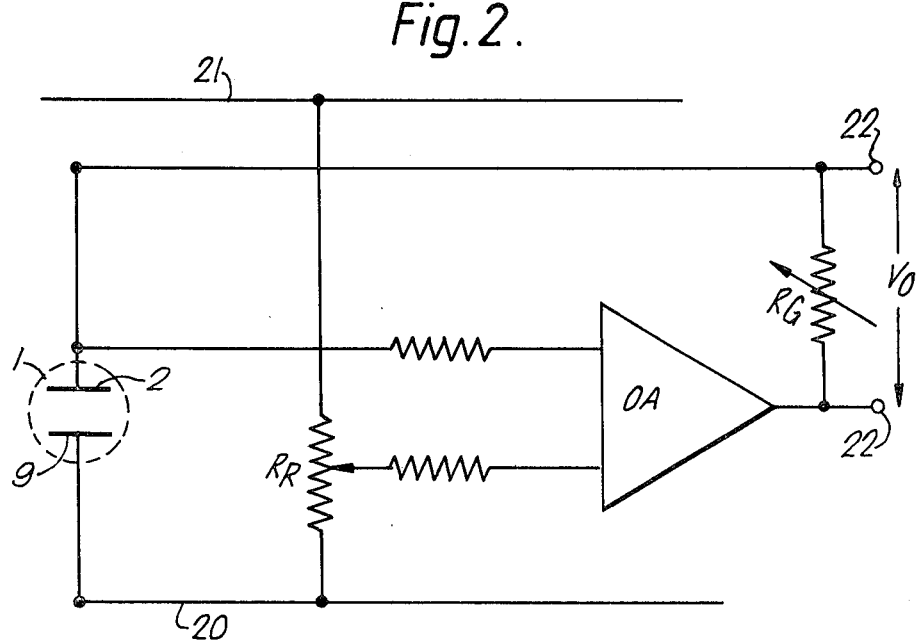
FIG. 2 is a diagram of a potentiostatic circuit for use with the cell of FIG. 1.

The choice of load circuit and mode of operation will depend upon the particular pair of sensing/counter electrodes chosen and whether or not a third reference electrode is used. There are some advantages in two-electrode cells in choosing identical couples for both electrodes, for example a pair of silver/silver oxide or a pair of mercury/mercury oxide electrodes. When sensing carbon dioxide the couple for the sensing electrode should initially be substantially in the oxidised state and the counter electrode substantially in reduced state. With such a matched pair of electrodes their potentials in the absence of carbon dioxide will be substantially equal. It is then possible to operate the sensor with a simple load resistor. However, even in this case, it can still be advantageous to make use of an electronic feed back circuit to hold the voltage of the sensor substantially at zero. The design of such potentiostatic circuits is well known and an example is shown in FIG. 2 of the accompanying drawings.

In the illustrated circuit a potential divider $R_R$, in conjunction with a stable reference voltage source, applied across conductors 20 and 21 is used to set the operating voltage of the sensing cell 1 at the desired level. An operational amplifier OA in conjunction with its feed back loop will then maintain this voltage constant. This circuit also acts as a current-to-voltage converter and converts the sensing cell current, which is its basic signal, to an output voltage signal $V_o$. By this means variations in signal current with variations in concentration of the gas being sensed may be followed, while the sensing cell voltage is maintained at a constant, pre-selected level. Scaling may be accomplished with a gain resistor $R_G$ connected across output terminals 22. The power supply circuit to the operational amplifier, which is standard, is not shown.

It is also perfectly possible to work with a combination of electrodes of different potential, for example, silver/silver oxide for the sensing electrode and lead for the counter electrode, which sensing cell will have a voltage of the order of 1.03 volts. In such cases it is necessary to use a potentiostatic circuit such as that described to maintain the sensor at or near its open circuit potential. Although in both the cases described above, namely either matched or unmatched electrode pairs, the sensor will normally be operated at or near its open circuit potential, i.e. its potential in the absence of carbon dioxide or other acidic or alkaline gases, it may be deliberately run with an offset base line either side of the open circuit potential, that is either with a background "charge" current or with a background "discharge" current. This background can be offset electronically in the measuring instrument.

Figure 3:
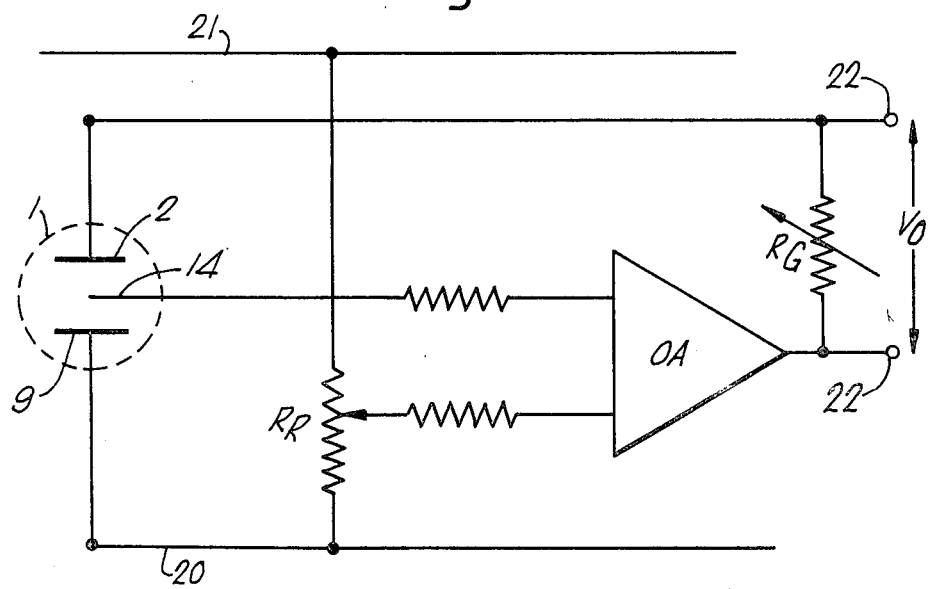
FIG. 3 is a diagram of a similar circuit for use when the cell includes a third or reference electrode.

FIG. 3 shows a basic potentiostatic circuit for use with a three-electrode cell, i.e. including a reference electrode 14. The components of the circuit are the same as in FIG. 2, the potential divider $R_R$ in this case serving to set the sensing electrode 9 at the desired potential with respect to the reference electrode 14 from which negligible current is drawn. The operational amplifier OA in conjunction with its feed back loop will maintain this potential constant, and the sensing cell current is converted to an output voltage signal $V_o$ as described with reference to FIG. 2.

This three electrode mode of operation has the advantage that the behaviour of the sensing electrode is not affected by any polarisation that may occur at the counter electrode.

Further benefits, for example concerned with long term stability, can be obtained in the following ways. Since during the periods that the sensor is in the presence of carbon dioxide there will be a net gain of carbon dioxide which will tend to lower the bulk pH of the electrolyte it is helpful if the electrolyte has a reasonable buffer capacity and/or the sensor contains a carbon dioxide "sink". The latter may be achieved for example by the use of an electrolyte containing carbonate or bicarbonate ions in conjunction with a counter electrode whose reaction product is carbonate or bicarbonate rather than oxide or hydroxide. We have found, for example, that this is the case with a lead counter electrode if the electrolyte pH is below about 13. The electrolyte may also contain a salt of a metal, e.g. barium or calcium, whose carbonate is less soluble than its hydroxide to act as a carbon dioxide sink, due to precipitation of the carbonate. This will also have the effect of giving excellent buffering action and the buffering capacity can be enhanced still further by the inclusion of extra solid salt of this type over and above its solubility.

It has been found surprisingly that the sensing electrode still responds even in the presence of strong buffers of this type. Over long periods of operation the precipitation of carbonate could lead to clogging of the sensing electrode. To substantially reduce this effect the sensor can include an anion exchange membrane close to the electrolyte side of the sensing electrode, the carbonate precipitating cation being confined substantially to the bulk electrolyte. Alternatively the salt in question e.g. calcium or barium hydroxide may be contained in a capsule bounded by an anion exchange membrane, said capsule being inserted in the electrolyte.

A further advantage in prolonging the active life of the sensor can be obtained by deliberately restricting the access of carbon dioxide to the sensing electrode by means of a diffusion barrier. Such a barrier may for example be formed from a non-porous plastic film. Diffusion through such films has, however, a high temperature co-efficient of the order of 2 to 3% per °C. and it is much more advantageous to make use of a gaseous diffusion barrier comprising a capillary or a porous membrane or a combination of these to give the advantage of a low temperature co-efficient.

Use of a capillary or capillaries providing a very severe diffusion restriction facilitates operation of the sensor in the intermittent sampling mode, described below, which has the advantage of reducing the rate of usage of active materials in the sensor and hence prolonging its useful life. Under static conditions the rate of diffusion is then so low that the resultant signal is insignificant. The measurement signal which is a function of the concentration of the gas being measured can then be generated by one of the sampling modes described below.

For example severely restrictive capillaries may form the two arms of a T-piece of which the vertical member provides no significant restriction to diffusion and is connected directly to the sensor. In operation, a sample of the gas to be tested is pumped along the cross member at a controlled flow rate for a given time to provide a pulse of sample gas to the sensor. The sampling time may be adjusted to suit the particular type of sensor and it has been found that in most cases sampling times between one and thirty seconds are suitable and may be controlled automatically by an electronic timer.

The dimensions of the capillaries can be chosen by trial and error depending on the particular electrode system of the sensor being used. In an example which has been found suitable in many cases, each arm of the T piece comprised a capillary of length 6 mm and of internal diameter about $5 \times 10^{-2}$ mm. Other capillaries having a similar ratio of cross sectional area to length are also suitable.

As an alternative the severely restrictive capillary may be fitted directly to the sensor itself, forming the vertical member of a T piece whose arms are of normal pipework. As mentioned originally, the rate of diffusion under static conditions is so low as to produce an insignificant resultant signal. Sampling is then carried out by producing periodic pulses of pressure, each of which has the effect of introducing a sample of gas through the capillary into the sensor. Although such a capillary provides a very severe restriction to diffusion, it will still offer relatively little resistance to bulk flow.

A method of operating such an arrangement is to cause the test gas to flow continuously along the cross member of the T piece and to block the outlet periodically so as to build up pressure to a value determined by a pressure relief valve. If the sample flow is intermittent, the pressure pulse may be generated by the inclusion of a flow restriction in the outlet.

Again the dimensions of the capillary can be chosen by trial and error. An example of a capillary which has been found suitable in many cases is one having a length of 3 mm and internal diameter of $5 \times 10^{-2}$ mm.

Generally speaking, it is found advantageous for the internal volume of the sensor to be somewhat greater when operating in a pressure-pulsing mode than when operating on a steady basis. For example, in the construction shown in FIG. 1, the thickness of the porous disc 11 may be made rather greater when intended for operation in a pressure-pulsing mode than when operating in the continuous mode. Alternatively, for the pressure pulsing mode, a spacing washer may be inserted between the porous disc 11 and the top cap 12.

It is found in practice that the magnitude of the resultant signal is dependent on the magnitude of the pressure pulse applied. A pressure pulse of the order of 6 KPa has been found to be suitable in many cases.

Details of the construction of electrochemical cells in accordance with the invention will now be described with reference to the following examples.

EXAMPLE I

A two electrode sensor made according to FIG. 1 had a silver oxide/silver sensing electrode 9 prepared by pre-charging a PTFE bonded silver powder electrode, a cellophane separator above the wicking separator 7, a lead counter electrode 2 and an electrolyte 3 of 4 molar potassium acetate containing excess solid calcium hydroxide. This was controlled at its open circuit potential using the circuit of FIG. 2, and the signal current was computed from the voltage measured across the gain resistor $R_G$ of known value. With an access hole 13 of 1.2 mm diameter and 2 mm length it gave a response when tested over the range 0–1% which was substantially linear to carbon dioxide concentration (95 μA in 0.5% $CO_2$). An identical sensor except that the access hole 13 was formed by a capillary of 0.5 mm bore and 2.5 mm length behaved similarly but with a lower signal of 9.4 μA in 0.5% $CO_2$.

EXAMPLE II

A two electrode sensor made according to FIG. 1 had silver oxide/silver electrodes for both sensing electrode 9 and counter electrode 2, an electrolyte 3 of 4M potassium carbonate and an access capillary of 0.5 mm bore and 2.5 mm length. When run with a simple 100 ohm load resistor it gave a signal of 122 μV in 0.5% $CO_2$, 63 μV in 0.25% $CO_2$ and 7 μV in ambient air.

EXAMPLE III

A two electrode sensor made according to FIG. 1 had silver oxide/silver electrodes for both sensing electrode 9 and counter electrode 2. An anion exchange membrane (AV-4T from Tokuyama Soda Ltd) which had previously been soaked in 4M potassium acetate was fitted just below the sensing electrode 9. The electrolyte confined below the anion exchange membrane was 4M potassium acetate containing excess solid barium hydroxide. When fitted with an access capillary of 0.5 mm bore and 3 mm length and run with a 100 ohm load resistor the sensor gave a response of 92 μV in 0.5% $CO_2$ and showed substantially linear behaviour over the range 0–5% $CO_2$.

EXAMPLE IV

A three electrode sensor made according to FIG. 1 had a silver oxide/silver sensing electrode 9, a silver oxide/silver reference electrode 14, a silver counter electrode 2 and an electrolyte 3 of 4M potassium acetate with excess solid calcium hydroxide. The two silver oxide/silver electrodes were formed in situ in the sensor from electrodes fabricated from PTFE bonded silver powder by connecting them together and charging the pair with a galvanostatic current of 250 μA for seven hours. The sensor was then connected to a three electrode potentiostatic circuit as shown in FIG. 3 which was adjusted to control the sensing electrode at zero volts with respect to the reference electrode. The signal current was computed from the voltage measured across the gain resistor $R_G$ of known value. When fitted with an access capillary of 0.9 mm bore and 3 mm length this sensor gave a response which was substantially linear when tested over the range 0–1% $CO_2$ (65 μA at 0.5% $CO_2$).

We claim:

1. A method of quantative detection of carbon dioxide by means of an electrochemical cell comprising a sensing electrode which is in contact with an electrochemical couple whose potential is pH dependent, a counter electrode without significant carbon dioxide access and an electrolyte in contact with both electrodes whose pH is such that it will change following absorption of the carbon dioxide being tested for and low impedance means for measuring the current flowing between the sensing and counter electrodes, this current being a measure of the concentration of the carbon dioxide being detected, wherein the flux to the sensing electrode of the carbon dioxide being tested for is controlled by a gas phase diffusion barrier which restricts the access of carbon dioxide and which comprises at least one narrow defined capillary passage or a combination thereof with a porous membrane for the diffusion of carbon dioxide, wherein the carbon dioxide being tested for is absorbed in the vicinity of the sensing electrode which is pH sensitive, thus changing the pH of the electrolyte in the vicinity of the pH sensitive sensing electrode and hence the potential of the sensing electrode, wherein as a consequence of said low impedance means for measuring the current flowing between the sensing and counter electrodes the potential change is restricted and current flows instead to redress pH imbalance, which current provides a signal dependent on the concentration of the carbon dioxide being tested for.

2. An electro-chemical cell for quantitatively detecting carbon dioxide comprising a sensing electrode to which access of the carbon dioxide to be tested is provided via a gas phase diffusion barrier which restricts the access of carbon dioxide and which comprises at least one narrow defined capillary passage or a combination thereof with a porous membrane for the diffusion of carbon dioxide, said sensing electrode being in contact with an electrochemical couple whose potential is pH dependent, a counter electrode without significant carbon dioxide access and an electrolyte in contact with both electrodes whose pH is such that it will change following absorption of the carbon dioxide being tested for and low impedance means for measuring current flowing between the sensing and counter electrodes, this current being a measure of the concentration of carbon dioxide being detected.

3. A cell as claimed in claim 2 including also a third, reference electrode without significant carbon dioxide access and means arranged to maintain said sensing electrode substantially at the potential characteristic of said electro-chemical couple in said electrolyte, in the absence of said carbon dioxide being detected.

4. A cell as claimed in claim 2 or claim 3 for the detection of carbon dioxide in which the pH of said electrolyte is between 4 and 14.

5. A cell as claimed in claim 2 or claim 3 for the detection of carbon dioxide in which the pH of said electrolyte is between 8 and 14.

6. A cell as claimed in claim 2 in which said pH-sensitive electro-chemical couple in conact with said sensing electrode is $Ag_2O/Ag$.

7. A cell as claimed in claim 2 in which said pH-sensitive electro-chemical couple in contact with said sensing electrode is $HgO/Hg$.

8. A cell as claimed in claim 3 in which said third reference electrode contains an $Ag_2O/Ag$ couple.

9. A cell as claimed in claim 8 in which said electrolyte contains a solid hydroxide of a metal selected from the group comprising barium, calcium and magnesium, said electrolyte being separated from said sensing electrode by an anion-exchange membrane.

10. A cell as claimed in claim 3 in which said third reference electrode contains an $HgO/Hg$ couple.

11. A cell as claimed in claim 10 in which said electrolyte contains a solid hydroxide of a metal selected from the group comprising barium, calcium and magnesium, said electrolyte being separated from said sensing electrode by an anion-exchange membrane.

12. A cell as claimed in claim 2 in which said electrolyte contains a solid hydroxide of a metal selected from the group comprising barium, calcium and magnesium.

* * * * *